_United States Patent_ [19]

von Bittera et al.

[11] Patent Number: 4,661,104

[45] Date of Patent: Apr. 28, 1987

[54] ACTIVE COMPOUND RELEASE SYSTEMS

[75] Inventors: Miklos von Bittera, Leverkusen; Rolf-Volker Meyer; Rolf Dhein, both of Krefeld, all of Fed. Rep. of Germany

[73] Assignee: Bayer Aktiengesellschaft, Leverkusen, Fed. Rep. of Germany

[21] Appl. No.: 681,976

[22] Filed: Dec. 14, 1984

[30] Foreign Application Priority Data

Dec. 28, 1983 [DE] Fed. Rep. of Germany ....... 3347277

[51] Int. Cl.$^4$ ........................ A61F 7/02; A61F 13/02; A61L 15/03; A61L 15/06
[52] U.S. Cl. ...................... 604/896; 424/78; 424/83; 428/156; 604/897
[58] Field of Search ................ 428/156; 604/897, 896; 424/78, 83

[56] References Cited

U.S. PATENT DOCUMENTS

| 3,742,951 | 7/1973 | Zafforoni . |
| 3,996,934 | 12/1976 | Zafforoni ........................... 604/897 |
| 4,031,894 | 6/1977 | Urquhart et al. .................... 604/386 |
| 4,201,211 | 5/1980 | Chandrasekoran et al. ....... 604/897 |
| 4,420,407 | 12/1983 | Otsuka et al. . |
| 4,455,146 | 6/1984 | Noda et al. ......................... 604/897 |

FOREIGN PATENT DOCUMENTS

| 2604718 | 8/1976 | Fed. Rep. of Germany . |
| 3007368 | 10/1980 | Fed. Rep. of Germany . |
| 3111734 | 1/1982 | Fed. Rep. of Germany . |
| 3119752 | 1/1982 | Fed. Rep. of Germany . |
| 3200369 | 8/1982 | Fed. Rep. of Germany . |
| 3317285 | 12/1983 | Fed. Rep. of Germany . |
| 3319469 | 11/1984 | Fed. Rep. of Germany . |
| 0132690 | 2/1985 | Fed. Rep. of Germany . |
| 2497457 | 7/1982 | France . |
| 56-2909 | 1/1981 | Japan .................................. 604/897 |
| 2021950 | 12/1979 | United Kingdom . |
| 2073588 | 10/1981 | United Kingdom . |
| 2095108 | 9/1982 | United Kingdom . |

_Primary Examiner_—Allan M. Lieberman
_Attorney, Agent, or Firm_—Sprung Horn Kramer & Woods

[57] ABSTRACT

In a therapeutic system such as a plaster for administration of an active compound through the skin and comprising a covering layer which is essentially impermeable to the active compound, an active compound reservoir layer and a protective layer which can be pulled off and which is essentially impermeable to the active compound, the improvement wherein the reservoir layer contain about 1–30% of active compound in an elastomer mixture comprising a predominantly amorphous olefinic (co)polymer with a glass transition temperature of <20° C., mixed with from 0 up to about 50% by weight of a polyisobutylene, polybutadiene oil and/or paraffin oil, and a tackifying resin. Thereby the active compound can be released in regulated relatively large quantity over a prolonged period of time.

24 Claims, 2 Drawing Figures

FIG.1

FIG.2

ACTIVE COMPOUND RELEASE SYSTEMS

The invention relates to a system for the release of an active compound onto the skin over a prolonged period, in particular to antiphlogistic medicinal plasters.

U.S. Pat. No. 4,031,894 describes medicinal plasters which have a reservoir of a mixture of polyisobutenes with very different molecular weights, in particular molecular weights of 35,000-50,000 and 1,000,000-1,500,000, and mineral oils.

These plasters are suitable only for active compounds which are administered in very small doses. Scopolamine is mentioned in the U.S. patent specification.

DOS (German Published Specification) No. 3,007,368 describes plaster compositions which contain active compounds and, as the polymer component, thermoplastic elastomers of the A-B-A or (A-B)$_n$X type, which largely contain vinylaromatics, preferably styrene, giving them thermoplastic processability.

Known active compound release systems, such as, for example, gels, ointments, known plasters and the like, allow only a limited absorption of active compound through the skin. The absorption depends on the base and the properties of the active compound.

An object of the present invention is to develop medicinal plasters with the aid of which regulated, relatively large therapeutically effective amounts of an active compound can be administered via the skin for a prolonged period. These plasters should be particularly suitable for the administration of antiphlogistics. They should be tolerated by the skin and with their aid it should be possible to administer high therapeutically effective doses of the active compound.

Surprisingly, it has now been found that corresponding plaster compositions with significantly increased rates of release of antiphlogistic active compounds are obtained if particular rubber-like, predominantly amorphous, olefinic (co)polymers with glass transition temperatures of <20° C., if appropriate also in combination with suitable diene rubbers or styrene/diene rubbers, are used as the polymer component.

The present invention thus relates to a therapeutic system for the administration of an active compound to the skin, containing a covering layer, a reservoir layer and a protective layer which can be pulled off, the reservoir layer containing a polymer consisting of rubber-like, predominantly amorphous, olefinic (co)-polymer with glass transition temperatures of <20° C., if appropriate also in combination with diene rubbers or styrene/diene rubbers, an entraining agent and a resin.

The invention also relates to plaster combinations containing an active compound reservoir which contains 2-15 parts by weight of antiphlogistic active compounds and which consists of 30-60% by weight of polymer, 30-60% by weight of entraining agents and 2-40% by weight of auxiliaries which influence the tackiness, the three components adding up to 100% by weight, characterised in that predominantly amorphous (co)polymers of at least one α-olefin or one cycloolefin, preferably of two different $C_2$—$C_{18}$—α—olefins, which can also be copolymerised with a further diolefin and have glass transition temperatures of <20° C., are used as the polymers, by themselves or as a mixture with up to 95% by weight, of the total amount of polymer, of known diene rubbers, which may also be copolymerised randomly or in blocks with α-olefins, preferably styrene.

The polymers which are to be used according to the invention are products which are known in principle and which are commercially available from various companies.

Examples of the polymers to be used according to the invention are amorphous polypropylene (predominantly atactic), amorphous polybut-1-ene (predominantly atactic), polyoctenamers (for example Vestenamer 8012 ® or Vestenamer A9 ® from Chem Werke Hüls AG) and ethylene/propylene copolymers which contain the amounts of the minor component incorporated either randomly or in blocks, preferably in blocks. Such products are described, for example, in Angew. Chem. 73, 186 (1961).

Examples of further polymers are copolymers of ethylene and/or propylene and other $C_4$—$C_{18}$—α—olefins, preferably of ethylene with $C_4$—$C_{12}$—α—olefins.

Examples of α-olefin copolymers copolymerized with dienes are products which are known as EPDM rubbers and which preferably consist of 20-90 parts by weight of ethylene, 10-80 parts by weight of propylene and 2-15 parts by weight (particularly preferably 4-10 parts by weight) of a non-conjugated diene. Of the large number of possible dienes, cyclopentadiene, ethylidenenorbornene and hexa-1,4-diene are particularly preferred diene components.

EPDM polymers which are particularly preferably to be employed in the context of the invention are those with molecular weights $M_w$ of 20,000 g/mol to about $M_w$ of $1 \times 10^6$ g/mol, preferably $M_w$ of up to 500,000 g/mol. The polymers to be used according to the invention can be used by themselves or in mixtures of several polymers of the polymers described, and also in combination with amorphous polyisobutenes which have a molecular weight distribution $M_w/M_n$ of 1.5-3.5, preferably 2.0-3.0.

The diene rubbers which are suitable for combination with the abovementioned polymers are likewise products which are known to the expert and which can be prepared on the basis of 1,3-dienes, such as butadiene, isoprene, piperylene and 2,3-dimethyl butadiene, preferably butadiene, in various ways which are known to the expert, it being possible to vary widely the nature of the double bonds in the polymer, depending on the choice of the metal catalyst (see, for example, Ullmanns Encyclopädie d. techn. Chemie (Ullmann's Encyclopaedia of industrial chemistry), 4th edition, volume 13, pages 602-611, Verlag Chemie, Weinheim/New York (1977).

Diene rubbers with more than 80% of cis-1,4-linkages are preferably used. Natural rubber is also suitable in the context of the parameters mentioned.

Examples of vinyl-aromatics which are suitable for combination with the diene rubbers are styrene, α-methylstyrene, vinyltoluenes, p-ethylstyrene, dimethylstyrenes and 4-vinyldiphenyl, preferably styrene. The diene rubbers modified with vinyl-aromatics are also products which are known, for example as "styrene/-butadiene rubber", and which can be prepared by known processes such that the vinyl-aromatic content is incorporated not only randomly but also partly or predominantly as a block structure in the diene rubber.

The amorphous (co)polymers from α-olefins or the EPDM rubbers by themselves are preferably used as the polymer components. In some particular cases, especially in order to prevent the separation of active compounds, for example by crystallization, in the long tern, a mixture with selected diene rubbers, preferably with up to 50% by weight of the total amount of polymer, may be advantageous.

Entraining agents in the context of the present invention are understood as meaning oils, fatty acid esters, triglycerides, alcohols and/or fatty acids.

Oils in the context of the present invention are understood as meaning high-boiling aliphatic, araliphatic and/or aromatic hydrocarbons, preferably paraffin oil, Purcellin oil, perhydrosqualene and solutions of microcrystalline waxes in the oils, and mineral oils, preferably oils with a boiling range between 150° C. and 400° C.; and furthermore unsaturated hydrocarbons with at least 16 C atoms, such as, for example, oligomers of monoolefins, such as tetraisobutylene, pentaisobutylene and hexaisobutylene, or liquid polymers of diene(monoene)(-co)polymers. Examples of liquid polymers of conjugated dienes are those of butadiene, isoprene, penta-1,3-diene, 2,3-dimethylbutadiene, copolymers of various dienes and liquid copolymers of a conjugated diolefin and small amounts of monoolefins, such as, for example, but-1-ene, isobutene, hex-1-ene, oct-1-ene and styrene, with molecular weights of 400 to 6,000, preferably 800 to 3,000, iodine numbers of 200 to 500 and viscosities of 100–10,000 cP at 50° C.

Liquid polybutadiene polymers which are at least 90% 1,4-linked, in which the content of cis-double bonds is more than 60% and which have molecular weights of 1,000 to 4,000 are particularly preferred.

Oils are also understood as meaning silicone oils of various viscosities, preferably with average molecular weights of 312 to 15,000, particularly preferably polydimethylsiloxanes.

Fatty acid esters are understood as meaning those which contain at least 12 C atoms, preferably 15 to 46 C atoms and particularly preferably 16 to 36 C atoms. By these there are understood, in particular: ethyl stearate, hexyl laurate, dipropylene glycol pelargonate, cetyl palmitate, isopropyl myristate, isopropyl palmitate, caprylic/capric acid esters of saturated fatty alcohols of $C_{12}$–$C_{18}$ chain length, isopropyl stearate, oleyl oleate, decyl oleate, ethyl oleate and synthetic duck uropygial gland fat, in each case individually or as a mixture.

Triglycerides are understood as meaning pure or mixed esters of glycerol and fatty acids of $C_8$–$C_{18}$ chain length, preferably caprylic and/or capric acid triglycerides.

Fatty acids are understood as meaning saturated or unsaturated fatty acids, preferably those with 12–24 C atoms, by themselves or as mixtures with one another, particularly preferably oleic acid.

Oils in the context of the invention are furthermore understood as meaning: sweet almond oil, avocado oil, sesame oil, castor oil, olive oil, grape seed oil, clove oil, groundnut oil, corn oil, hazelnut oil, jojoba oil, carthama oil and wheatgerm oil, in each case by themselves or as a mixture.

Resins in the context of the present invention are understood as meaning rosin, dehydrogenated rosin, glycerol esters of dehydrogenated rosin, glycerol esters of rosin gum, hydrogenated rosin, glycerol esters of hydrogenated rosin, pentaerythritol esters of hydrogenated rosin, methyl esters of hydrogenated rosin, polymerized rosin, glycerol esters of polymerized rosin, terpene resins, coumarone/indene resins, hydrogenated petroleum resins, rosin modified by maleic anhydride and rosin derivatives, $C_5$-petroleum resins and half-esters of styrene/maleic acid copolymers, by themselves or as mixtures with one another. Polyterpene resins of alpha- or beta-pinene or modified glycerol esters of rosin are particularly preferred. Depending on the properties required in respect of tackiness and adhesion to the part onto which the resulting plaster is to be applied, these resins can be used either by themselves or in combination with one another.

Antiphlogistics in the context of the present invention are one or more antiphlogistics of the general formula I and/or II.

Antiphlogistics of the general formula I have the following structure:

wherein
$R_1$–$R_5$ can be identical or different and denotes hydrogen, halogen, lower alkyl or substituted alkyl,
X denotes N or CH and
Y denotes hydrogen, metal ions, alkyl or substituted alkyl.

Halogen denotes fluorine, chlorine or bromine, preferably chlorine and/or bromine and particularly preferably chlorine. Lower alkyl is preferably alkyl with 1–6 C atoms, particularly preferably 1–4 C atoms, and substituted alkyl $R_1$–$R_5$ preferably denotes trihalogenoalkyl, particularly preferably trifluoromethyl. Metal ions are understood as meaning the ions of alkali metals, alkaline earth metals or aluminum, preferably sodium. Substituted alkyl Y preferably denotes alkoxyalkyl, hydroxyalkyl, hydroxyalkoxyalkyl or trihalogenoalkyl, in which the number of C atoms is 1 to 6 and the alkyl chain can be straight or branched.

Antiphlogistics which are preferably used are those of the general formula I in which
$R_3$ and $R_4$ denote hydrogen,
X denotes nitrogen or a CH group,
Y denotes hydrogen, $C_1$—$C_4$—alkyl or substituted $C_1$—$C_4$—alkyl, hydroxyalkyl or hydroxyalkoxyalkyl with 1 to 6 atoms and
$R_1$, $R_2$ and $R_5$ denote hydrogen, chlorine, $C_1$—$C_4$—alkyl or trifluoromethyl.

Particularly preferred antiphlogistics of the general formula I are those in which
X represents a CH group,
Y denotes hydrogen or hydroxyalkoxyalkyl with 1 to 6 C atoms and
$R_1$, $R_2$ and $R_5$ denote methyl, hydrogen, trifluoromethyl or chlorine.

The following antiphlogistics are very particularly preferred.

N—(α,α,α-Trifluoro-m-tolyl)-anthranilic acid = flufenamic acid

N—(2,3-Xylyl)-anthranilic acid

-continued

2-(2,6-Xylidino)-nicotinic acid 2-(2-Hydroxyethoxy)-ethyl
N—(α,α,α-trifluoro-m-tolyl)-anthranilate = etofenamate Antiphlogistics in the context of the present invention are furthermore antiphlogistics of the general formula II having the structure:

in which
R denotes hydrogen, lower alkyl or substituted alkyl,
Ar denotes aryl, heteroaryl, substituted aryl or substituted heteroaryl,
(n+m) denotes an integer and has the value zero, 1 or 2, and
p denotes zero or 1,
with the condition that Ar does not denote aryl or heteroaryl if n, m and p have the value of zero, and esters or amides thereof.

R preferably denotes lower alkyl radicals with 1–6 C atoms, preferably 1–4 C atoms, substituted alkyl, alkoxyalkyl or trihalogenoalkyl; aryl or heteroaryl, for example phenyl, naphthyl, thiophenyl, pyrrolyl, indenyl, indolyl, benzothiazinyl or phenothiazinyl.

Substituents for aryl or heteroaryl are alkyl, preferably straight-chain or branched alkyl with up to 6 C atoms, alkoxy, hydroxyalkyl, acyl, hydroxyl, acetoxy, benzoyl, substituted benzoyl, phenyl, substituted phenyl, phenoxy, halogen, phenylalkenyl and phenylalkyl.

The esters are alkyl esters with 1–6 C atoms, preferably 1–4 C atoms in the alcohol component, particularly preferably methyl, ethyl, i- and n-propyl, substituted alkyl, for example β-hydroxyethyl, esters of glycolic acid. The amides can also contain lower alkyl or substituted alkyl radicals in the grouping —CO—NH₂ instead of one or both of the amide hydrogens.

The following antiphlogistics of the general formula II are particularly preferred:

2-Hydroxybenzoic acid

2-Acetoxybenzoic acid

2′,4′-Difluoro-4-hydroxy-3-biphenylcarboxylic acid

2-Hydroxybenzamide

[2-(aminocarbonyl)phenxoy]-acetic acid

4-Allyloxy-3-chlorophenylacetic acid = alclofenac

2-[(2,6-Dichlorophenyl)amino]-phenylacetic acid

10-Methyl-phenothiazin-2-yl-acetic acid = metiazinic acid

1-Methyl-5-(p-toluoyl)-pyrrol-2-yl-acetic acid

D—2-(6-Methoxy-2-naphthyl)-propionic acid = naproxen

-continued

2-(p-Isobutylphenyl)-propionic acid

2-(3-Phenoxyphenyl)-propionic acid

2-(m-Benzoylphenyl)-propionic acid = ketoprofen

2-[4-(1-Oxo-2-isoindolinyl)-phenyl]-propionic acid = indoprofen

2-(2-Fluorobiphenyl-4-yl)-propionic acid 3-(4-Biphenylcarbonyl)-propionic acid

2-(5-Benzoyl-2-thienyl)-propionic acid 1-(p-Chlorobenzoyl)-5-methoxy-
2-methylindole-3-acetic acid = indometracin

-continued

1-(p-Chlorobenzoyl)-5-methoxy-2-
methylindole-3-acetoxyacetic acid = acemetacin

(Z)—5-Fluoro-2-methyl-1-[(3-methyl-
sulfinyl)phenyl]-methylene)-1H—indene-3-acetic acid

4-Butyl-1,2-diphenyl-3,5-pyrazolidine-dione = phenylbutazone

4-(3-Methyl-but-2-enyl)-
1,2-diphenyl-pyrazolidine-3,5-dione = feprazone

2-(4'-Chlorophenyl)-α-methyl-5-
benzoxazoleacetic acid = benoxaprofen

N—(2-thiazolyl)-2-methyl-4-hydroxy-
2H—1,2-benzothiazine-3-carboxamide 1,2-dioxide N—(2-pyridinyl)-2-methyl-4-hydroxy-
2H—1,2-benzothiazine-3-carboxamide
1,1-dione (keto/enole mixture)

and alkyl esters and substituted alkyl esters thereof.

Either one or more of the abovementioned antiphlogistics of the general formulae I and II can be incorporated into the plasters.

The anitphlogistics can be incorporated into the reservoir layer in an amount of 1-30% by weight, preferably 2-20% by weight. The % by weight given relates to the total reservoir.

Other active substances or cooling or fragrance-releasing substances, preferably methyl salicylate, glycol salicylate, salicylic acid, menthol, peppermint oil, camphor, thymol, Acrinol, scopola extract, chloropeniramine maleate, benzyl nicotinate, capsicum extract, nonylvanillylamide and capsaicin, can also additionally be added to these antiphlogistics.

If necessary, additives and fillers, for example anti-ageing agents, antioxidants and reinforcing fillers, can be added to the plasters according to the invention as long as the gel-like properties are not destroyed.

Know active compound release systems, such as, for example, gels, ointment bases and plasters, release about 0.5-5 mg of active compound in 4 hours. In contrast, the therapeutic system according to the invention described above releases up to 18 mg of active compound in 4 hours, with a significantly greater bioavailability. The rate of release of the active compound from the systems according to the invention can be adjusted to almost any desired value by changing the polymer content, the entraining agent or the resin.

The reservoir containing the active compound and the plaster based thereon can be produced, for example, as follows: the plaster bases (polymer, resin and entraining agent) are introduced into a suitable dissolving vessel and are dissolved in benzine, with stirring. clear to slightly turbid solution 1 results. The active compound component is also dissolved in a suitable solvent, and the solution is added to polymer solution 1.

The resulting solution 2 containing active compound is applied uniformly to siliconized paper and drawn to a film. The coated paper with the plaster base is dried in air for 24 hours and then kept in a circulating air drying cabinet at 40° C. for 1 hour.

The rates of release of active compound are determined in an absorption model desribed in more detail in the experimental section. (FIGS. 1 and 2).

Figure 1:
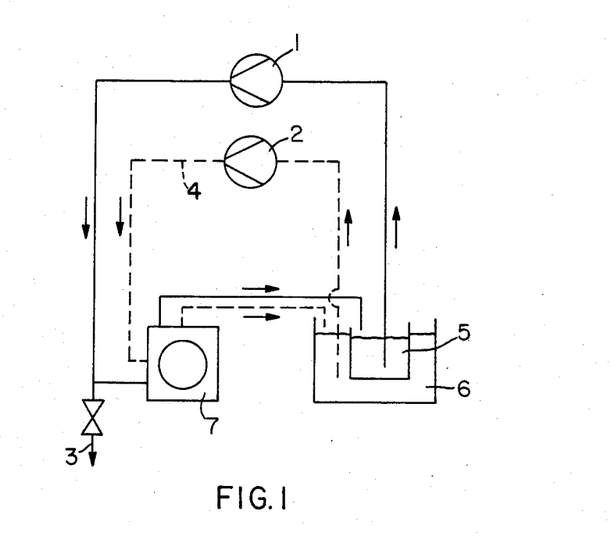

In FIG. 1 (1) represent a hose pump for the acceptor, (2) a hose pump for heating, (3) sample withdrawal, (4) circulation for heating liquid, (5) the acceptor medium, (6) the heating vessel and (7) the resorption cell with membrane.

Figure 2:
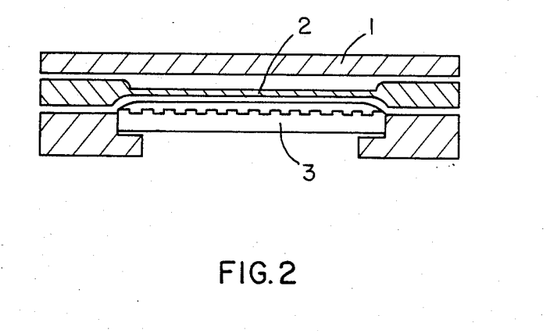

In FIG. 2 (1) represents an opaque cell material, (2) a membrane and (3) a viewing window of glass, also corrugated plate for the acceptor medium.

Testing in Vitro of the Release of the Plasters
According to the Invention

All the plasters were produced in the same manner, with 10% of active compound component, from polymer, entraining agent, resin and, if appropriate, solvent (benzine, hexane- or a hexane/toluene mixture). The particular proportions used are given in the recipe descriptions.

For this, all the components were dissolved or suspended. Acetone and/or ethanol were chiefly used as the solvents for the active compound.

These solutions or suspensions were processed to films 50-150 μm thick.

| Experimental parameters: | |
|---|---|
| acceptor medium | mixture of water, ethanol, PVP and sorbitan fatty acid ester |
| volume of the acceptor medium | 200 ml |
| temperature of the acceptor medium | 35-36° C. |
| pump capacity | 16 ml/minute (apparatus constant) |
| membrane | the film described in Example 3 of DE-OS (German Published Specification) 3,312,735 was used as the membrane |
| Absorption area | 33.18 cm² (cell constant) |

The acceptor medium was heated to the required temperature in a stock vessel and pumped around the absorption cells via tubes. Samples were withdraw between the pump and the absorption cells. Sampling was effected at specified intervals of time. In each case 6 ml of sample were withdrawn and measured by spectrophotometry. The acceptor liquid was not replaced, since this would means a dilution of the remainder.

Calculation of the Results

A calibration curve was first recorded for the particular active compound component, with the aid of which the active compound concentration (mg or %) in the individual samples was determined from the extinction values measured for the individual samples. The extinctions were measured by UV spectroscopy.

To calculate the "relative absorption" (proportion of "absorbed" active compound of the total content of the plaster in %), it is necessary to know the amount of active compound employed. The content of active compound of a defined plaster size (33.18 cm²) is known from the production of the plaster.

The concentration of active compound in the sample was determined from the extinction values measured for the individual samples, with the aid of a calibration line or the factor determined therefrom.

$$M_i(t) = V_t \cdot C_i + M_F(t) \text{ [mg]}$$

$$M_F(t) = \sum_{i=0}^{i=n-1} (V_D \cdot C_i) \text{ [mg]}$$

$M_i(t)$: amount of drug released up to time t [mg] $V_t$: volume of the acceptor at time t [ml] $C_1$: active compound concentration in the sample in question [mg/ml] $M_F(t)$: amount of active compound removed up to time t [mg] $V_D$: sample volume [ml] n: number of samples up to time t t: duration of the experiment Description of the Preparation The active compound release systems according to the invention were produced as follows: the mixture of polymer, resin and entraining agent were prekneaded in a Z-kneader at a temperature of 120° to 150° C. When the mass was a homogeneous melt, the active compound was homogeneously incorporated, while gassing with nitrogen. The melt containing active compound was applied to the carrier film (kneader).

The active compound release systems according to the invention were dissolved in a solvent mixture and the solution was applied to the carrier film and then dried (solution).

Example series A: standard (not according to the invention)

In this series of experiments, a styrene/isoprene/styrene TR block copolymer ("Cariflex TR 1107 from Shell Chemical Company) was used as the polymer, thinly liquid paraffin was used as the entraining agent and a polyterpene resin from β-pinene was used as the tackifying resin.

The styrene/isoprene/styrene TR block copolymer plaster containing 10% of active compound was used as the reference standard in all the further experiments.

The precise composition of the plaster base is given in Table 1. The plaster was produced as described above. The rates of release are described in Table 2.

TABLE 1

| Composition of the standard formulation Styrene/isoprene/styrene/TR | |
|---|---|
| block copolymer | 36.0 g |
| Thinly liquid paraffin | 45.0 g |
| Polyterpene resin from β-pinene | 9.0 g |
| Etofenamate | 10.0 g |

TABLE 2

| | Release from the experimental standard series as a function of time | | | | | | | |
|---|---|---|---|---|---|---|---|---|
| | Amount of etofenamate released in mg/hour | | | | | | | Amount of etofenamate weighed |
| | 0.5 | 1 | 1.5 | 2 | 3 | 4 | % | out in mg |
| Standard 10% | 1.44 | 2.16 | 2.70 | 3.24 | 4.63 | 4.81 | 21.20 | 22.77 |

Example series B

In this series of experiments, the composition of the polymers was varied. The precise description of the polymers is given in Table 3.

The plasters were produced as described above.

The amounts of all the polymers listed in Table 3 were varied in accordance with the following scheme, the paraffin oil and resin content remaining constant:

| | A1 | A2 |
|---|---|---|
| Polymer | 36.0 g | 45.0 g |
| Thinly liquid paraffin oil | 45.0 g | 37.5 g |
| Polyterpene resin from β-pinene | 9.0 g | 7.5 g |
| Etofenamate | 10.0 g | 10.0 g |

The rates of release are described in Table 4.

TABLE 3

Example series B: description of the polymers used.

The two first numbers designate the polymer, the designation of the formulation being given instead of x (see above, A1 or A2).

No. 01×polyoctenamer; cis/trans ratio about 20:80, viscosity number I at 25° C.: 120 mL/g 02×EPDM—terpolymer with about 45% by weight of propylene, ethylidenenorbornene as the diene component, iodine number about 13, Mooney plasticity (1+4) minutes running time, 100° C.: 45

03×as 02, but with about 30% by weight of propylene, iodine number about 13, Mooney plasticity (1+4) minutes running time, 100° C.: 35

04×as 03, grafted with 9% of styrene/butadiene, iodine number about 15

05×EPDM—terpolymer (3% of ethylidenenorbornene) with about 60 parts by weight of propylene, iodine number about 7, Mooney plasticity 65

06×as 05, with 6% of ethylideneorbornene, iodine number about 12, Mooney plasticity 55

07×as 05, with 6% of dicyclopentadiene, iodine number about 12, Mooney plasticity 40

TABLE 4

| Example series B: release as a function of the time | | | | | | | | |
|---|---|---|---|---|---|---|---|---|
| | Etofenamate released (mg) in hours | | | | | | | Amount of etofenamate weighed out |
| No. | 0.5 | 1 | 1.5 | 2 | 3 | 4 | % | in mg |
| Standard | 1.44 | 2.16 | 2.70 | 3.24 | 4.63 | 1.81 | 21.20 | 22.77 |
| 01 A1 | 3.57 | 5.05 | 6.20 | 7.55 | 9.48 | 10.82 | 54.15 | 19.99 |
| 01 A2 | 2.45 | 5.71 | 7.53 | 8.83 | 11.92 | 14.00 | 45.73 | 30.62 |
| 02 A1 | 4.39 | 5.82 | 7.45 | 9.03 | 11.57 | 12.63 | 56.12 | 22.50 |
| 02 A2 | 4.79 | 6.48 | 8.44 | 10.02 | 12.85 | 14.88 | 53.58 | 27.78 |
| 03 A1 | 3.67 | 5.45 | 7.12 | 8.31 | 10.28 | 11.67 | 43.70 | 26.71 |
| 03 A2 | 3.83 | 6.05 | 8.16 | 10.96 | 12.65 | 12.65 | 47.02 | 26.90 |
| 04, A1 | 2.86 | 4.19 | 5.29 | 6.64 | 9.63 | 9.78 | 50.14 | 19.51 |
| 04 A2 | 2.65 | 3.64 | 4.70 | 5.71 | 7.06 | 8.71 | 49.13 | 17.73 |
| 05 A1 | 3.82 | 6.45 | 9.23 | 10.99 | 13.72 | 15.67 | 67.91 | 23.09 |

TABLE 4-continued

Example series B: release as a function of the time

| No. | \multicolumn{6}{c}{Etofenamate released (mg) in hours} | | Amount of etofenamate weighed out in mg |
|---|---|---|---|---|---|---|---|---|
| | 0.5 | 1 | 1.5 | 2 | 3 | 4 | % | |
| 05 A2 | 3.72 | 6.34 | 8.41 | 10.59 | 13.46 | 15.54 | 47.86 | 32.47 |
| 06 A1 | 4.90 | 6.68 | 8.35 | 9.89 | 12.18 | 13.61 | 55.40 | 24.56 |
| 06 A2 | 3.47 | 5.69 | 8.33 | 9.71 | 12.19 | 14.10 | 47.01 | 29.99 |
| 07 A1 | 5.71 | 7.54 | 9.41 | 11.17 | 13.60 | 14.94 | 54.28 | 27.53 |
| 07 A2 | 3.93 | 6.65 | 8.52 | 10.65 | 13.35 | 15.21 | 52.70 | 28.86 |

Example series C: Variation of the liquid components

The liquid component of the formulations chosen from Example series B was changed in composition according to the following scheme, the remainder of the recipe being retained.

| | B1 | B2 |
|---|---|---|
| Polymer | as in Example series H | |
| Liquid component | Polybutadiene oil of molecular weight 1,500 | Polybutadiene oil of molecular weight 1,500 + thinly mobile paraffin oil 1:1 |
| Etofenamate | 10% | 10% |

The precise composition of the plaster bases are given in Table 5 and the rates of release are given in Table 6.

TABLE 5

Example series C: Composition of the formulations

| No. | Polymer | liquid polybutadiene oil | thinly mobile paraffin oil | Resin | Etofenamate |
|---|---|---|---|---|---|
| 02A2 | 45% | — | 37.5% | 7.5% | 10% |
| 02B1 | 45% | 37.5% | — | 7.5% | 10% |
| 02B2 | 45% | 18.75% | 18.75% | 7.5% | 10% |
| 07A1 | 36% | — | 45% | 9% | 10% |
| 07B1 | 36% | 45% | — | 9% | 10% |
| 07B2 | 36% | 22.5% | 22.5% | 9% | 10% |
| 07A2 | 45% | — | 37.5% | 7.5% | 10% |
| 07B1 | 45% | 37.5% | — | 7.5% | 10% |
| 07B2 | 45% | 18.75% | 18.75% | 7.5% | 10% |

TABLE 6

Example series C: Release as a function of time

| No. | \multicolumn{6}{c}{Etofenamate released (mg) in hours} | | Amount of etofenamate weighed out in mg |
|---|---|---|---|---|---|---|---|---|
| | 0.5 | 1 | 1.5 | 2 | 3 | 4 | % | |
| Standard | 1.44 | 2.16 | 2.70 | 3.24 | 4.63 | 4.81 | 21.20 | 22.77 |
| 02A2 | 4.79 | 6.48 | 8.44 | 10.02 | 12.85 | 14.88 | 53.58 | 27.78 |
| 02B1 | 3.11 | 4.69 | 6.18 | 7.57 | 10.04 | 11.95 | 42.52 | 28.10 |
| 02B2 | 3.52 | 5.15 | 7.16 | 8.60 | 11.12 | 13.24 | 42.14 | 31.42 |
| 07A1 | 5.71 | 7.54 | 9.41 | 11.17 | 13.60 | 14.94 | 54.28 | 27.53 |
| 07B1 | 2.04 | 3.68 | 5.54 | 6.80 | 9.89 | 12.28 | 35.00 | 35.08 |
| 07B2 | 1.99 | 3.47 | 5.24 | 6.59 | 9.37 | 11.46 | 40.97 | 27.96 |
| 07A2 | 3.93 | 6.65 | 8.52 | 10.65 | 13.35 | 15.21 | 52.70 | 28.86 |
| 07B1 | 2.55 | 4.73 | 6.60 | 8.31 | 11.46 | 13.62 | 44.23 | 30.80 |
| 07B2 | 2.55 | 4.58 | 6.64 | 8.22 | 11.41 | 13.88 | 42.57 | 32.59 |

TABLE 7

Recipes with a changed resin content

| No. | Polymer | Paraffin | Resin | Etofenamate |
|---|---|---|---|---|
| 02A2 | 45% | 37.5% | 7.5% | 10% |
| 02C1 | 43.2% | 36% | 10.8% | 10% |
| 02C2 | 41.5% | 34.6% | 13.9% | 10% |

TABLE 8

Release with the changed resin content

| N. | \multicolumn{6}{c}{Etofenamate released (mg) in hours} | | Amount of etofenamate weighed out in mg |
|---|---|---|---|---|---|---|---|---|
| | 0.5 | 1 | 1.5 | 2 | 3 | 4 | % | |
| Standard | 1.44 | 2.16 | 2.70 | 3.24 | 4.63 | 4.81 | 21.20 | 22.77 |
| 02A2 | 4.79 | 6.48 | 8.44 | 10.02 | 12.85 | 14.88 | 53.58 | 27.78 |
| 02C1 | 3.42 | 5.74 | 8.04 | 9.57 | 11.73 | 13.42 | 51.59 | 26.01 |
| 02C2 | 2.19 | 3.87 | 5.31 | 6.43 | 8.54 | 10.05 | 32.68 | 30.76 |

Example 1 (solution)

| Polyoctenamer; cis/trans ratio about 20:80 | 45.0 g |
|---|---|
| Thinly mobile paraffin | 37.5 g |
| Polyterpene resin from β-pinene | 7.5 g |
| Etofenamate | 10.0 g |

Release: 14.0 mg (45.73%) after 4 hours

Example 2 (solution)

| EPDM terpolymer with about 45% by weight of propylene, ethylidene-norbornene as the diene component, Mooney viscosity (1 + 4) minutes running time 100° C.: 45 | 45.0 g |
|---|---|
| Thinly mobile paraffin | 37.5 g |
| Polyterpene resin from β-pinene | 7.5 g |
| Etofenamate | 10.0 g |

Release: 14.88 mg (53.58%) after 4 hours

Example 3 (solution)

| EPDM terpolymer with about 30% by weight of propylene, Mooney viscosity (1 + 4) minutes running time 100° C.: 35 | 36.0 g |
|---|---|
| Thinly mobile paraffin | 45.0 g |
| Polyterpene resin from β-pinene | 9.0 g |
| Etofenamate | 10.0 g |

Release: 11.67 mg (43.7%) after 4 hours

Example 4 (solution)

| EPDM terpolymer with about 30% by weight of propylene, grafted with 9% of styrene/butadiene | 36.0 g |
|---|---|
| Thinly liquid paraffin | 45.0 g |
| Polyterpene resin from β-pinene | 9.0 g |
| Etofenamate | 10.0 g |

Release: 9.78 mg (50.14%) after 4 hours

Example 5 (solution)

| EPDM terpolymer (3% of ethylidene-norbornene) with about 60 parts by weight of propylene, Mooney viscosity (1 + 4) minutes running time 100° C.: 65 | 36.0 g |
|---|---|
| Thinly liquid paraffin | 45.0 g |
| Polyterpene resin from β-pinene | 9.0 g |
| Etofenamate | 10.0 g |

Release: 15.67 mg (67.91%) after 4 hours

Example 6 (solution)

| EPDM terpolymer (6% of ethylidene-norbornene), Mooney viscosity (1 + 4) minutes running time 100° C.: 55 | 36.0 g |
|---|---|
| Thinly liquid paraffin | 45.0 g |
| Polyterpene resin from β-pinene | 9.0 g |
| Etofenamate | 10.0 g |

Release: 13.61 mg (55.4%) after 4 hours

Example 7 (solution)

| EPDM terpolymer with 6% of dicyclopentadiene, Mooney viscosity (1 + 4) minutes running time 100° C.: 40 | 36.0 g |
|---|---|
| Thinly mobile paraffin | 45.0 g |
| Polyterpene resin from β-pinene | 9.0 g |
| Etofenamate | 10.0 g |

Release: 14.94 mg (54.28%) after 4 hours

Example 8 (solution)

| Polyoctenamer; cis/trans ratio about 20:80 | 36.0 g |
|---|---|
| Thinly liquid paraffin | 22.5 g |

TABLE 8-continued

| Release with the changed resin content | |
|---|---|
| Decyl oleate | 22.5 g |
| Modified glycerol ester of rosin | 9.0 g |
| Acemetacin | 10.0 g |
| Release: 12.72 mg (52.71%) after 4 hours | |
| Example 9 (solution) | |
| EPDM terpolymer with 5% of dicyclopentadiene, Mooney viscosity (1 + 4) minutes running time 100° C.: 40 | 36.0 g |
| Decyl oleate | 22.5 g |
| Thinly mobile paraffin | 22.5 g |
| Modified glycerol ester of rosin | 9.0 g |
| Ketoprofen | 10.0 g |
| Release: 10.21 mg (47.3%) after 4 hours | |
| Example 10 (solution) | |
| EPDM terpolymer with 6% of dicyclopentadiene, Mooney viscosity (1 + 4) minutes running time 100° C.: 40 | 36.0 g |
| Isopropyl myristate | 22.5 g |
| Thinly liquid paraffin | 22.5 g |
| Polyterpene resin from α-pinene | 9.0 g |
| Acemetacin | 10.0 g |
| Release: 10.21 mg (44.5%) after 4 hours | |

It will be understood that the specification and examples are illustrative but not limitative of the present invention and that other embodiments within the spirit and scope of the invention will suggest themselves to those skilled in the art.

We claim:

1. In a therapeutic system including an active compound, an upper covering layer that is essentially impermeable to the active compound, an active compound reservoir layer and a protective layer that can be pulled off and that is essentially impermeable to the active compound, the improvement which comprises the reservoir layer containing 1 to 30% of an active compound, said active compound being an antiphlogistic agent in an elastomeric mixture, said elastomic mixture comprising predominantly amorphous olefinic polymers or copolymers, said polymers or copolymers having glass transition temperatures of less than 20° C., the mixture containing (a) (i) two different ($C_2$-$C_{18}$) α-olefins or cycloolefins, (ii) or the mixture containing two different ($C_2$-$C_{18}$) α-olefins or cycloolefins copolymerized with a diolefin alone, with up to 95% by weight of the total amount of polymer being a diene rubber or a diene rubber copolymerized with an α-olefin, said diene rubber-containing copolymer having a molecular weight from 20,000 to $1 \times 10^6$ g/mole, (b) an entraining agent selected from the group consisting of polyisobutylene oil, polybutadiene oil, paraffin oil and mixtures thereof and (c) a tackifying resin.

2. A therapeutic system according to claim 1, wherein as the active compound is 2 to 30% by weight of an antiphogistic in the reservoir.

3. A therapeutic system according to claim 2, wherein the reservoir containing active compound comprises about 30-60% by weight of polymer or copolymer, 30-60% by weight of entraining agent and 2-40% by weight of resin, in addition to the active compound.

4. A therapeutic system according to claim 1, wherein the polymer or copolymer comprises an EPDM rubber comprising about 20-90% by weight of ethylene, 10-80% by weight of propylene and 2-15% by weight of a non-conjugated diene.

5. A therapeutic system according to claim 1, wherein the polymer comprises a polyoctenamer.

6. A therapeutic system according to claim 4, wherein the polymer or copolymer is mixed with a diene rubber.

7. A therapeutic systems according to claim 2, wherein the entraining agent comprises at least one of a paraffin oil and liquid polybutadiene oil.

8. A therapeutic system according to claim 1, wherein the active compound is selected from the group consisting of antiphlogistics of the formula $$Ar \!-\! (C)_p \!-\! (CH)_n \!-\! (CH_2)_m \!-\! COOH,$$
$$\phantom{Ar \!-\! (}\overset{O}{\|}\phantom{)_p \!-\! (}\overset{R}{|}$$

in which
$R_1$–$R_5$ each independently is hydrogen, halogen, lower alkyl or substituted alkyl,
X is N or CH,
Y is hydrogen, a metal ion, alkyl or substituted alkyl,
R is hydrogen, lower alykyl or substituted alkyl,
Ar is aryl, heteroaryl, substituted aryl or substituted heteroaryl,
n and m each is an integer and together total zero, 1 or 2, and
p is zero or 1,
with the proviso that Ar is not aryl or heteroaryl if n, m and p each is zero.

9. A system according to claim 1, wherein the active compound is etofenamat.

10. A system according to claim 1, wherein the active compound is ketoprofen.

11. A system according to claim 1, wherein the active compound is acematacin.

12. A system according to claim 1, wherein the active compound is indoprofen.

13. A system according to claim 1, wherein the active compound is indometacin.

14. A treatment system according to claim 1, wherein the active compound is contained in an amount of 2 to 20% by weight.

15. A therapeutic system according to claim 1, wherein the entraining agent is contained in an amount of up to 50% by weight.

16. A therapeutic system according to claim 1, wherein the polymer or copolymer is selected from the group consisting of amorphous polypropylene, amorphous polybut-1-ene, polyoctenamers and ethylene/propylene copolymers.

17. A therapeutic system according to claim 1, wherein the α-olefin is a $C_4$ to $C_{18}$ α-olefin.

18. A therapeutic system according to claim 1, wherein the α-olefin is a $C_4$ to $C_{12}$ α-olefin.

19. A therapeutic system according to claim 4, wherein the weight % of the propylene is 4 to 10%.

20. A therapeutic system according to claim 4, wherein the non-conjugated diene is selected from the group consisting of cyclopentadiene, ethyldene-norbornene and hexa-1,4-diene.

21. A therapeutic system according to claim 4, wherein the molecular weight is up to 500,000 g/mol.

22. A therapeutic system according to claim 1, wherein the diene rubber is prepared on the basis of a diene which is selected from the group consisting of butadiene, isoprene, piperylene and 2,3-dimethylbutadiene.

23. A therapeutic system according to claim 1, wherein the diene rubber has more than 80% of cis-1,4-linkages.

24. A thereapeutic system according to claim 1, wherein a vinyl aromatic is combined with the diene rubber, said vinyl aromatic being selected from the group consisting of styrene, α-methylstyrene, vinyltoluenes, p-ethylstyrene, dimethylstyrenes and 4-vinyldiphenyl.

* * * * *

UNITED STATES PATENT AND TRADEMARK OFFICE
CERTIFICATE OF CORRECTION

PATENT NO. : 4,661,104

DATED : April 28, 1987

INVENTOR(S) : Miklos von Bittera, et al.

It is certified that error appears in the above-identified patent and that said Letters Patent is hereby corrected as shown below:

| | |
|---|---|
| Title Page, under "U.S. Patent Documents" | Lines 1 and 2 delete "Zafforoni" and substitute --Zaffaroni--; Line 5 delete "4,420,407" and substitute --4,420,470-- |
| Title Page, Abstract, line 8 | Delete "contain" and substitute --contains-- |
| Col. 2, line 42 | Delete "dimethyl butadiene" and substitute --dimethylbutadiene-- |
| Col. 2, line 67 | Delete "tern" and substitute --term-- |
| Col. 7, line 68 | Delete "indometracin" and substitute --indometacin-- |
| Col. 9, line 24 | Delete "1,2-dioxide" and substitute --1,1-dioxide-- |
| Col. 10, line 10 | Before "clear" insert --A-- |
| Col. 11, line 27 | Delete "$C_1$" and substitute --$C_i$-- |
| Col. 12, line 36 | After "120" delete "mL/g" and substitute --ml/g-- |
| Col. 13, line 21 | Delete "series H" and substitute --series B-- |
| Col. 12, line 36 | After "ml/g" insert --glass transition temperatures $T_G$-65°C.-- |

UNITED STATES PATENT AND TRADEMARK OFFICE
CERTIFICATE OF CORRECTION

PATENT NO. : 4,661,104

DATED : April 28, 1987

INVENTOR(S) : Millos von Bittera, et al.

It is certified that error appears in the above-identified patent and that said Letters Patent is hereby corrected as shown below:

Col. 13,
"TABLE 7", line 65     Insert --Example series D: Variation of the resin content--

Signed and Sealed this

Twelfth Day of July, 1988

Attest:

DONALD J. QUIGG

Attesting Officer     Commissioner of Patents and Trademarks

UNITED STATES PATENT AND TRADEMARK OFFICE
CERTIFICATE OF CORRECTION

PATENT NO. : 4,661,104

DATED : April 28, 1987

INVENTOR(S) : Miklos von Bittera, et al.

It is certified that error appears in the above-identified patent and that said Letters Patent is hereby corrected as shown below:

Col. 15, line 38   Delete "elastomic" and substitute --elastomeric--

Signed and Sealed this

Twenty-seventh Day of September, 1988

*Attest:*

DONALD J. QUIGG

*Attesting Officer*   *Commissioner of Patents and Trademarks*